United States Patent [19]

Bywater et al.

[11] Patent Number: 5,008,248

[45] Date of Patent: Apr. 16, 1991

[54] VETERINARY COMPOSITIONS FOR THE TREATMENT OF SCOURS AND DEHYDRATION

[75] Inventors: Robert J. Bywater; Robert J. Dupe, both of Surrey, England

[73] Assignee: Beecham Group p.l.c., Epsom, England

[21] Appl. No.: 474,635

[22] Filed: Jan. 30, 1990

Related U.S. Application Data

[63] Continuation of Ser. No. 930,498, Nov. 14, 1986, abandoned.

[30] Foreign Application Priority Data

Nov. 18, 1985 [GB] United Kingdom ................. 8528307
Mar. 7, 1986 [GB] United Kingdom ................. 8605689

[51] Int. Cl.$^5$ ..................... A61K 31/195; A61K 31/70
[52] U.S. Cl. ...................................... 514/23; 514/884; 514/867; 424/442; 426/2
[58] Field of Search .......................... 514/23, 884, 867; 424/442; 426/2

[56] References Cited

U.S. PATENT DOCUMENTS 3,898,328 8/1975 Beigler et al. ...................... 514/23
4,164,568 8/1979 Bywater ............................. 514/867

FOREIGN PATENT DOCUMENTS 0112061 6/1984 European Pat. Off. .
0114104 7/1984 European Pat. Off. ............. 514/23

OTHER PUBLICATIONS

Bywater; Am. J. Vet. Res. 38(12): 1983-1988, (1977).
Nisshin Flour Milling Co., Chemical Abstracts 97:168904z, (1982).
Meiji Milk Products Co.; Chemical Abstracts 98:204438g, (1983).
U.S. FDA; Chemical Abstracts 99:128190y, (1983).

*Primary Examiner*—Ronald W. Griffin
*Assistant Examiner*—Nancy S. Carson
*Attorney, Agent, or Firm*—Hopgood, Calimafde, Kalil, Blaustein & Judlowe

[57] ABSTRACT

A veterinary composition comprising 75-85% of an actively absorbed monosaccharide, from 3.5 to less than 5% of an actively absorbed naturally occurring amino acid, 5-10% of one or more citrate salts. The composition is useful in the treatment of diarrhoea in domestic animals such as calves.

14 Claims, No Drawings

VETERINARY COMPOSITIONS FOR THE TREATMENT OF SCOURS AND DEHYDRATION

This application is a continuation of application Ser. No. 930,498, filed Nov. 14, 1986, now abandoned.

The present invention relates to veterinary compositions useful for treating disorders in domestic animals, and in particular to compositions useful for treating diarrhoea (e.g. scours) in domestic animals and to the use of such compositions in the treatment of diarrhoea by rehydration.

A common and highly debilitating disease affecting young domestic animals such as calves and piglets is diarrhoea. Diarrhoea causes severe dehydration which in turn causes a significant weight loss in the animal and can in severe cases lead to death. It is believed that often the diarrhoea symptoms are caused by a toxin or toxins of bacterial origin so that one method for the treatment of diarrhoea is the administration of anti-bacterial agents. Considerable success can be achieved by using such anti-bacterial agents as ampicillin or amoxycillin but there are occasions when an alternative therapy is required.

British Patent Specification No. 1,581,826 discloses compositions for the treatment of diarrhoea in domestic animals which combine effectiveness with ease of formulation, palatability and useful stability. Such compositions comprise an actively absorbed monosaccharide, an actively absorbed naturally occurring amino acid, and citric acid or a salt thereof.

New compositions have now been discovered, which possess all the advantages of those disclosed in British Patent Specification No. 1,581,826, but which in addition exhibit a significantly improved ability to absorb water from the intestinal tract of treated domestic animals such as calves, piglets, horses, dogs and cats. In addition, the compositions of the present invention may be used to advantage to correct acidosis in such animals. Certain of the compositions hereinunder described may also be used to provide more energy per dose than compositions previously disclosed.

Accordingly, the present invention provides a veterinary composition comprising 60-85% of an actively absorbed mono-saccharide, from 3.5 to less than 7.5% of an actively absorbed naturally occurring amino acid, and 0.5-10% of an agent which is citric acid and/or one or more salts thereof.

All percentages used herein are calculated on a weight/total weight basis.

The present invention also provides a process for the preparation of a veterinary composition, which process comprises mixing the above ingredients in the necessary proportions.

Active absorption (or active transport) is well known to the skilled man, as are the monosaccharides and amino acids which are actively absorbed. In this regard the reader is referred to standard text books such as 'Medicinal Physiology' by Guyton (published by W. B. Saunders and Company), 4th Edition, pages 769 to 771. Of course, whether or not a particular monosaccharide or amino acid is actively absorbed may also readily be determined by experiment, as for example described in Wilson T. H. 'Intestinal Absorption'(Saunders, Philadelphia, 1962).

To be actively absorbed, monosaccharides must have (a) at least six carbon atoms in their chain; (b) a D-pyranose ring structure; and (c) an intact hydroxyl group at carbon 2. Thus suitable examples of monosaccharides for use in this invention include the naturally occurring D-pyranoses such as glucose and galactose. Other examples of suitable monosaccharides include naturally occurring D-pyranoses that have been chemically modified whilst retaining the necessary structural features (a), (b) and (c). Examples of such modified monosaccharides include $C_{2-7}$ acylated and $C_{1-4}$ alkylated derivatives, such as acetyl, methyl, ethyl and n- and iso-propyl derivatives. Specific examples include α-methyl glucoside, 3-O-methyl glucose and 6-deoxygalactose.

Preferably the monosaccharide will be glucose or galactose. The monosaccharide of choice for use in this invention is glucose (e.g. dextrose). The monosaccharide used may be anhydrous, for example anhydrous glucose, or a hydrated form may be used, for example glucose monohydrate.

Suitable examples of actively absorbed naturally occurring amino acids include neutral amino acids such as glycine and alanine and basic amino acids such as arginine. Preferably the amino acid is glycine.

Suitable examples of salts of citric acid include sodium or potassium salts, such as mono-, di- or tri-sodium, or mono-, di- or tri-potassium citrate, and acid salts, such as disodium hydrogen citrate and dipotassium hydrogen citrate. The citric acid and salts thereof may be anhydrous or hydrated.

The veterinary compositions of the invention will normally contain 5 to 25% electrolytes. Suitable electrolytes for such inclusion include salts containing ions such as sodium, potassium, calcium, magnesium, chloride, phosphate, gluconate, sulphate, bicarbonate, carbonate and the like. Other favoured electrolytes for inclusion in the compositions include tripotassium phosphate, potassium chloride and the like.

Advantageously the compositions include a buffering agent such as potassium dihydrogen phosphate, dipotassium hydrogen phosphate and the like. A particularly suitable buffering agent is potassium dihydrogen phosphate which normally accounts for 0.5-5% of the composition, usually 1-3% of the composition. Suitably the composition is so formulated that the pH of an aqueous solution for administration to a diarrhoeic animal is in the range 5.0-7.0, preferably 5.5-6.5.

Another preferred electrolyte for inclusion in the composition of the invention is sodium chloride which will normally account for 4-20% of the composition, for example 5-10% of the composition.

The monosaccharide is defined as representing 60-85% of the composition. More suitably it will represent 70-85%, for example 75-85% of the composition. Often the monosaccharide will represent at least 75% of the composition. Similarly, while the amino acid in the composition can represent from 3.5 to less than 7.5% of the composition, more suitably it will represent 3.5-6.0% of the composition, for example 3.5-5% of the composition.

From the foregoing description, it will be seen that particularly suitable veterinary compositions of the invention comprise 70-85% of glucose or galactose, 3.5-6% of glycine, alanine or arginine, 0.5-10% of citric acid and/or one or more salts thereof, 1-3% of potassium dihydrogen phosphate and 5-10% of sodium chloride.

One type of composition that is particularly suitable comprises citric acid and one or more salts thereof.

Preferably such compositions contain a mixture of citric acid, sodium citrate and potassium citrate, together representing 0.5-10% of the composition, often 5-10% of the composition. Advantageously, such compositions will contain 0.5-5% of citric acid and 0.1-9.5% of a mixture of tri-sodium and tri-potassium citrate. Conveniently the citric acid, sodium citrate and potassium citrate are in hydrated form.

One preferred composition of the invention comprises 70-85% of glucose, 3.5-6% of glycine, 0.5-2% of citric acid, 5-9.5% of a mixture of tri-sodium and tri-potassium citrates, 5-10% of sodium chloride, and 1-3% of potassium dihydrogen phosphate.

A particularly preferred composition comprises at least 75% glucose.

A second type of veterinary composition that is particularly suitable comprises one or more salts of citric acid but does not contain any citric acid that is not in the form of a salt.

Another preferred composition of the invention thus comprises 70 to 85% of glucose 3.5 to 6% of glycine, 0.5 to 10% of sodium chloride. Such compositions often include 1 to 3% of potassium dihydrogen phosphate. Advantageously such compositions contain a mixture of di-sodium hydrogen citrate, tri-sodium citrate and tri-potassium citrate representing 0.5 to 10% of the composition. Conveniently these citric acid salts are in hydrated form.

These compositions suitably contain at least 75% monosaccharide.

A particularly preferred composition of this type comprises 80-83% of glucose monohydrate, 3.5-4% of glycine, 5-7% of sodium chloride, 1.5-2% of potassium dihydrogen phosphate, 0.5-1% of tri-sodium citrate dihydrate, 2.0 -2.5% of di-sodium hydrogen citrate sesquihydrate and 4.0-4.5% of tri-potassium citrate monohydrate.

If desired the compositions of this invention can contain other substances such as vitamins, minerals, buffers, excipients or the like in conventional manner.

In general the compositions of this invention will be in the form of a dry powder, for example one which is readily soluble in water. However in an alternative aspect the compositions of this invention will comprise an aqueous solution containing dissolved therein the previously defined solutes in the previously defined relative proportions.

The powders of this invention may be prepared by mixing together the individual components in conventional manner. Once mixed the composition may be put into sachets or other conventional containers. It is frequently advantageous to separate the mono-saccharide component from the other components of the composition. This may be effected by using separate sachets, or a twin pack comprising double sachets or other double containers. In such cases components other than the mono-saccharide may be mixed and filled into one sachet, or one half of the double sachet, and the mono-saccharide may be filled into the other sachet, or other half of the double sachet. In such form the compositions of the invention have been found to be particularly stable.

Accordingly the present invention also provides a twin pack comprising one container holding 60-85% of an actively absorbed mono-saccharide and a separate container holding from 3.5 to less than 7.5% of an actively absorbed naturally occurring amino acid and 0.5 to 10% of an agent which is citric acid and/or one or more salts thereof.

The invention also provides a process for preparing a twin pack, which process comprises filling one container with 60-85% of an actively absorbed mono-saccharide and filling a separate container with 3.5 to less than 7.5% of an actively absorbed naturally occurring amino acid and 0.5 to 10% of an agent which is citric acid and/or one or more salts thereof.

The percentage figure given for each ingredient indicates the relative proportion by weight of that ingredient with respect to the total weight of the composition of the invention contained in the twin pack.

The composition of the invention will normally be administered to the diarrhoeic animal in the form of an aqueous solution, by the oral route, using a stomach tube if necessary. Such solutions may for example contain 20 to 45 g/liter of the composition suitably 25 to 40 g/liter. In general calves will have administered to them from 4 to 6 liters per day of such solutions while piglets will normally be administered from a quarter of a liter to one liter per day. The solutions may be administered ad libitum, or in two to four or more equal doses per day, or by any other similar conventional regime.

Under certain circumstances, suitably prepared and sterilized aqueous solutions of the composition of the invention may be administered intravenously.

A further aspect this invention provides a method of treating diarrhoea in domestic animals, which method comprises administering to the animal suffering from diarrhoea a composition of this invention dissolved in an aqueous medium.

It will be realised that in the treatment of severely scouring animals anti-bacterial agents may be administered in conjunction with the compositions of the invention. Examples of suitable anti-bacterial agents for such use include ampicillin, amoxycillin and tetracyclines.

The skilled person will realise that the effective absorption properties found with the compositions of the invention when dissolved in aqueous media will enable them to be used with advantage whenever absorption of liquids by animals is a problem. For example the compositions may be used in treating the general dehydration found in post-operative conditions in animals such as dogs and cats. They may also be administered with advantage to stressed animals, such as recently purchased calves and the like.

It has been found that the compositions of the present invention, dissolved in a suitable volume of water, e.g. 60–100 g./200 ml, may also be used for the treatment of hypoglycaemia associated with ovine or bovine ketosis.

Accordingly, a further aspect of this invention provides a method of treating hypoglycaemia associated with ovine or bovine ketosis, which method comprises administering to the animal suffering therefrom a composition of this invention dissolved in an aqueous medium.

The following Examples illustrate the invention.

EXAMPLE 1

A total of 77.45 g of the following composition was prepared by mixing together the following ingredients in dry powder form:

|  | Grams | % of total |
| --- | --- | --- |
| Glucose monohydrate | 62.7 | 80.96 |
| Glycine | 3.0 | 3.87 |

-continued

|  | Grams | % of total |
| --- | --- | --- |
| Sodium chloride | 4.6 | 5.94 |
| Potassium dihydrogen phosphate | 1.4 | 1.81 |
| Citric acid monohydrate | 0.5 | 0.65 |
| Tri-sodium citrate dihydrate | 2.0 | 2.58 |
| Tri-potassium citrate monohydrate | 3.25 | 4.19 |

The whole composition was then dissolved in 2 liters of water.

EXAMPLE 2

For storage, the composition according to Example 1 was prepared in the same manner but the glucose monohydrate (62.7 g) was filled into one sachet and the remaining ingredients (14.75 g) were filled into a second sachet.

EXAMPLE 3

A total of 77.41 g of the following composition was prepared by mixing together the following ingredients in dry powder form:

|  | Grams | % of total |
| --- | --- | --- |
| Glucose monohydrate | 62.7 | 81.00 |
| Glycine | 3.0 | 3.87 |
| Sodium chloride | 4.6 | 5.94 |
| Potassium dihydrogen phosphate | 1.4 | 1.81 |
| tri-sodium citrate. $2H_2O$ | 0.66 | .85 |
| disodium hydrogen citrate. $1\frac{1}{2} H_2O$ | 1.80 | 2.33 |
| tri-potassium citrate. $1H_2O$ | 3.25 | 4.20 |

The composition was dissolved in 2 liters of water for use.

For storage the glucose monohydrate (62.7 g) was filled in one sachet and the remaining ingredients (14.71 g) were filled into a second sachet.

BIOLOGICAL DATA

Acute absorption studies were carried out on the composition of Example 1 after it had been dissolved in 2 liters of water.

The method used was to anaesthetise male calves (weight approx. 40 kg.), and to perform a laparotomy, identifying points along the small intestine situated at 5 sites, about 5%, 20%, 50%, 70% and 95% of the distance from the pyloric sphincter to the ileo-caecal valve. At each of these points, series of short lengths of intestine were isolated by ligatures. Phenol red was added to the solution under investigation and the resulting solution was then injected into the intestinal loops. The water movement was followed by measuring changes in phenol red concentration.

The results obtained were as shown in the Table below:

TABLE

| % Distance Pyloric Sphincter to the Ileo-caecal valve | Water Absorbed (ml/cm/30 min) | Standard Error of the Mean (S.E.M.) |
| --- | --- | --- |
| 5 | 0.20 | ±0.03 |
| 20 | 0.19 | ±0.05 |
| 50 | 0.27 | ±0.025 |
| 70 | 0.22 | ±0.05 |
| 95 | 0.13 | ±0.03 |

We claim:

1. A veterinary composition, comprising by weight:
   75-85% of an actively absorbed monosaccharide,
   3.5-5% of an actively absorbed naturally occurring amino acid,
   1-3% of a buffering agent,
   5-10% of an electrolyte, and
   5-10% of one or more citrate salts, said composition not containing any citric acid that is not in the form of a salt.

2. A composition according to claim 1 in which the monosaccharide is glucose or galactose.

3. A composition according to claim 1 in which the amino acid is glycine, alanine or arginine.

4. A composition according to claim 1 additionally comprising 5-25% sodium chloride.

5. A composition according to claim 1 additionally comprising a buffering agent such that the pH of an aqueous solution for administration to a diarrhoeic animal is in the range 5.0-7.0.

6. A composition according to claim 1 comprising 75-85% of glucose or galactose, 3.5-5.0% of glycine, alanine or arginine, 5-10% of one or more citrate salts, 1-3% of potassium dihydrogen phosphate and 5-10% of sodium chloride.

7. The composition according to claim 1 comprising 80-83% of glucose monohydrate, 3.5-4% of glycine, 0.5-1% of tri-sodium citrate dihydrate, 2.0-2.5% of di-sodium hydrogen citrate sesquihydrate, 4.0-4.5% of tri-potassium citrate monohydrate, and additionally comprising 5-7% sodium chloride and 1.5-2% of potassium dihydrogen phosphate.

8. A composition according to claim 1 in aqueous solution.

9. A composition according to claim 1 additionally comprising an antibacterial agent.

10. A twin pack comprising one container holding 75-85% of an actively absorbed monosaccharide and a separate container holding from 3.5 to 5% of an actively absorbed naturally occurring amino acid and 5-10% of one or more citrate salts, said twin pack not containing any citric acid that is not in the form of a salt.

11. A method of treating diarrhoea in domestic animals, which method comprises administering to the animal suffering from diarrhoea a therapeutically effective amount of the composition as defined in claim 1 dissolved in an aqueous medium.

12. A method of treating hypoglycaemia associated with ovine or bovine ketosis, which method comprises administering to the animal suffering therefrom a therapeutically effective amount of the composition as defined in claim 1 dissolved in an aqueous medium.

13. A veterinary composition comprising 60-85% of an actively absorbed monosaccharide, from 3.5 to less than 7.5% of an actively absorbed naturally occurring amino acid, and 0.5-10% of an agent which is selected from the group consisting of
   (a) one or more veterinarily acceptable citrate salts, and
   (b) a mixture of citric acid and one or more veterinarily acceptable citrate salts.

14. The veterinary composition of claim 13, wherein in (b) the mixture comprises from 0.5-5% of citric acid and from 0.1-9.5% of the veterinarily acceptable citrate salt,
   said percent being be weight based upon the composition.

* * * * *